United States Patent [19]
Childers

[11] Patent Number: 5,906,794
[45] Date of Patent: May 25, 1999

[54] CONTINUOUS-OPERATION, CLOSED LOOP DECONTAMINATION SYSTEM AND METHOD

[75] Inventor: Robert W. Childers, New Port Richey, Fla.

[73] Assignee: American Sterilizer Company, Mentor, Ohio

[21] Appl. No.: 08/664,980

[22] Filed: Jun. 14, 1996

Related U.S. Application Data

[60] Provisional application No. 60/000,321, Jun. 15, 1995.
[51] Int. Cl.⁶ .................................. A61L 2/20; A61L 2/24
[52] U.S. Cl. .............................. 422/28; 422/30; 422/111; 422/305
[58] Field of Search .................................. 422/292, 294, 422/299, 302, 307, 900, 905, 28, 30, 29, 174, 177, 305, 111; 219/430, 439

[56] References Cited

U.S. PATENT DOCUMENTS

| | | | |
|---|---|---|---|
| 4,435,194 | 3/1984 | Picard et al. ................................. | 55/96 |
| 4,509,505 | 4/1985 | Mercey et al. ........................... | 128/1 B |
| 4,843,867 | 7/1989 | Cummings ................................... | 73/23 |
| 4,898,713 | 2/1990 | Picard ........................................ | 422/3 |
| 4,909,999 | 3/1990 | Cummings et al. ..................... | 422/298 |
| 4,956,145 | 9/1990 | Cummings et al. ....................... | 422/28 |
| 4,992,247 | 2/1991 | Foti ......................................... | 422/304 |
| 5,173,258 | 12/1992 | Childers ..................................... | 422/27 |
| 5,258,162 | 11/1993 | Andersson et al. ........................ | 422/28 |
| 5,445,792 | 8/1995 | Rickloff et al. ........................... | 422/28 |
| 5,508,009 | 4/1996 | Rickloff et al. ......................... | 422/292 |

FOREIGN PATENT DOCUMENTS

| | | |
|---|---|---|
| 298 694 | 1/1989 | European Pat. Off. . |
| WO 88/04939 | 7/1988 | WIPO . |
| WO 89/06140 | 7/1989 | WIPO . |
| WO 91/05573 | 5/1991 | WIPO . |

*Primary Examiner*—Elizabeth C. Kemmerer
*Assistant Examiner*—David S. Romeo
*Attorney, Agent, or Firm*—Fay, Sharpe, Beall, Fagan, Minnich & McKee

[57] ABSTRACT

The invention provides an optimized method and system for conducting a continuous-operation, closed-loop, flow-through vapor phase decontamination. By the method, a liquid decontaminant is vaporized and delivered into, through and out of a sealable chamber by means of a carrier gas that is recirculated in a closed-loop conduit circuit. After leaving the chamber, the vapor is decomposed and the carrier gas is partially and selectively dried in response to the monitored temperature, relative humidity, and decontaminant vapor concentration in the chamber. The degree of drying is particularly selected in response to these chamber parameters to maintain a predetermined percent saturation of the decontaminant vapor in the chamber.

18 Claims, 4 Drawing Sheets

CONTINUOUS-OPERATION, CLOSED LOOP DECONTAMINATION SYSTEM AND METHOD

This application claims the benefit of U.S. Provisional Application No. 60/000,321, filed Jun. 15, 1995.

FIELD OF THE INVENTION

The present invention relates generally to a system and method of vapor-phase decontamination, and more particularly to a flow-through system and method of decontamination using a vapor phase decontaminant.

BACKGROUND OF THE INVENTION

Reusable medical, pharmaceutical, and biological instruments are generally sterilized before each use. Additionally, reusable containers employed in medical, pharmaceutical, and biological applications, such as glove boxes and incubators, are generally sterilized before each use. In facilities and applications where these types of instruments and containers are used several times a day, it is important to achieve sterilization efficiently and economically.

Several different methods have been developed for delivering a vapor phase sterilant to an enclosure or chamber for sterilizing the load (e.g., medical instruments) or interior thereof. In one option, the "deep vacuum" approach, a deep vacuum is used to pull liquid sterilant into a heated vaporizer; once vaporized, the sterilant is propelled by its vapor pressure into an evacuated and sealed chamber. In another option, the "flow-through" approach, vaporized sterilant is mixed with a flow of carrier gas that serves to deliver the sterilant into, through and out of the chamber, which may be at slightly negative or positive pressure.

In addition, methods have been developed for optimizing vapor phase sterilization in a deep vacuum and/or flow-through system. U.S. Pat. No. 4,956,145 discloses a deep vacuum method of vapor phase sterilization in which a predetermined concentration of hydrogen peroxide sterilant is maintained in an evacuated, sealed chamber. The amount of sterilant injected into the chamber is regulated or adjusted to account for the decomposition of hydrogen peroxide sterilant vapor into water and oxygen in the closed system over time. A different approach is disclosed in U.S. Pat. Nos. 5,445,792 and 5,508,009, incorporated by reference herein, wherein a predetermined percent saturation is maintained in an open, flow-through sterilization. The rate of hydrogen peroxide vapor injection into a carrier gas is regulated or adjusted in response to predetermined characteristics of the carrier gas.

Also, several systems and apparatus have been developed for conducting vapor phase sterilization. An open flow-through system designed to handle the disposition of residual sterilant vapors is disclosed in U.S. Pat. No. 4,909,999 and is incorporated by reference herein. That system can be integrally associated with or releasably connected to a sealable container.

U.S. Pat. No. 5,173,258, which is incorporated by reference herein, discloses another flow-through system in which vapor phase hydrogen peroxide is introduced into a recirculating, closed flow of carrier gas. The hydrogen peroxide vapor is introduced and maintained at a predetermined concentration selected to optimize the sterilization cycle. The system includes a dryer to dehumidify the recirculating flow, preferably to at least about 10% relative humidity, and thereby prevent moisture build-up resulting from the decomposition of hydrogen peroxide vapor over time. By eliminating moisture build-up, the system can maintain the sterilization chamber at higher concentrations of vapor phase hydrogen peroxide sterilant for longer periods of time (i.e., the predried gas will accept more of the sterilant vapor). Further, to avoid condensation of the sterilant, the relative humidity in the chamber is preferably reduced (e.g., to at least about 10%) prior to introducing sterilant vapor. After decontamination is complete, the enclosure may be rehumidified or conditioned if desired for the selected application.

The foregoing methods and systems are effective at sterilization and/or provide an enhanced sterilization cycle. There exists, however, a need for further improvement or a more efficient sterilization.

SUMMARY OF THE INVENTION

The present invention provides an optimized method of conducting a closed-loop, flow-through vapor phase decontamination. The invention also provides a continuous-operation, closed-loop system for carrying out the method.

In the method, a flow of carrier gas is recirculated in a closed-loop conduit circuit that leads into, through, and out of a sealable chamber. The invention can be used for flow rates ranging from only one or two standard cubic feet per minute (SCFM) to flow rates of thousands of SCFM. A liquid decontaminant is vaporized and delivered into the carrier gas flow entering the chamber, and then converted to a form suitable for disposal after exiting the chamber.

The carrier gas preferably comprises air. The liquid decontaminant preferably comprises aqueous hydrogen peroxide, and the vaporized hydrogen peroxide decontaminant vapor is preferably converted to water and oxygen with a catalytic converter.

To prevent condensation resulting from unacceptable moisture build-up over time, the carrier gas flow is dried before reentering the chamber. However, in the method of the present invention, the carrier gas is partially and selectively dried in response to the monitored temperature, relative humidity, and decontaminant vapor concentration in the chamber. The degree of drying is particularly selected in response to these chamber parameters to maintain a predetermined percent saturation of the decontaminant vapor in the chamber during decontamination.

As a result, the water vapor content or humidity of the carrier gas entering the chamber may be higher (i.e., the carrier gas is dried to a lesser extent) during decontamination than was previously permitted or sought. As mentioned, in the prior closed-loop system disclosed in U.S. Pat. No. 5,173,258, the carrier gas humidity in a closed loop system is continuously reduced to maximize the amount of decontaminant vapor accepted into the carrier gas (or to maximize the decontaminant vapor concentration, rather than the vapor percent saturation).

The selective drying of the carrier gas is preferably carried out by selectively routing a portion of the carrier gas flow through an air dryer positioned upstream of the chamber inlet port and selectively bypassing a remaining portion of the carrier gas flow around the air dryer. The chamber parameters which provide feed-back for selecting the degree of drying can be monitored directly by temperature, relative humidity, and concentration sensors placed in the chamber, or indirectly by other means, as hereinafter described.

The flow-through vapor phase decontamination system of the invention includes a sealable chamber having an inlet port and an outlet port. A conduit circuit is fluidly connected to the chamber ports to provide a closed-loop flow path for recirculating a carrier gas into, through, and out of the chamber. The system also includes a blowing unit and an adjustable drying unit, each fluidly connected to the conduit circuit. The blowing unit serves to push or force the carrier gas around the closed-loop flow path. The adjustable drying unit serves to dry selectively the carrier gas flow entering the chamber.

The drying unit preferably comprises a variable valve having a first flow path and a second flow path, and a regenerative air dryer having an inlet port and an outlet port. The air dryer is positioned downstream of the two-way valve. A first fluid flow line connects the first flow path to the dryer inlet port, while a second fluid flow line bypasses the dryer and connects to the conduit circuit downstream of the drying unit. By varying the amount of flow through the first and second valve flow paths, a selected portion of the carrier gas flow can be routed to bypass the dryer. In this way, the humidity of the carrier gas can be regulated or adjusted (i.e., the carrier gas can be selectively dried) to maintain a predetermined percent saturation of decontaminant vapor in the chamber as the decontamination cycle proceeds.

The blowing unit preferably comprises a first blower positioned upstream and a second blower positioned downstream of the drying unit. More preferably, the blowers can be adjusted based on feedback from flow sensors to provide a slightly negative or positive pressure within the chamber.

The system also includes a liquid vaporizer unit for delivering a vaporized liquid decontaminant into the carrier gas flow. The vaporizer unit is fluidly connected to the conduit circuit between the drying unit and the chamber inlet port. In addition, the system includes a converter for converting the decontaminant vapor to a form suitable for disposal, and fluidly connected to the conduit circuit downstream of the chamber outlet port. When the decontaminant vapor is hydrogen peroxide, the converter preferably comprises a catalytic converter for decomposing hydrogen peroxide to water and oxygen.

The system also includes a processing unit for monitoring the following three parameters within the chamber during decontamination: 1) the temperature, 2) the relative humidity, and 3) the vapor concentration. The degree of drying of the carrier gas is selected in response to these three parameters, to maintain a predetermined percent saturation of the decontaminant vapor during decontamination.

The processing unit may include a temperature sensor, relative humidity sensor, and a vapor concentration sensor positioned within the chamber to monitor directly the internal chamber temperature, relative humidity, and vapor concentration. Alternatively, the processing unit may include means for indirectly monitoring these parameters, as hereinafter described.

BRIEF DESCRIPTION OF THE DRAWINGS

The present invention can be better understood by reference to the drawings in which.

DETAILED DESCRIPTION OF THE INVENTION

The method of the present invention can be used to optimize the efficacy of vapor phase decontamination in a closed, flow-through cycle. The term "decontamination" shall be understood to include sterilization, disinfection, and sanitization. For the purpose of describing the preferred embodiments herein the objective discussed will be sterilization.

The sterilant vapor preferably comprises hydrogen peroxide generated from 30–35% by weight aqueous hydrogen peroxide solution. The carrier gas preferably comprises air. It is contemplated that other condensible gas sterilants and other inert gas carriers, such as nitrogen, may also be used. For purposes of describing the preferred embodiments, the carrier gas and the sterilant vapor discussed will be respectively air and vapor phase hydrogen peroxide generated from an aqueous hydrogen peroxide solution.

In the method, a flow of carrier gas is recirculated in a closed-loop conduit circuit that leads into, through, and out of a sealable sterilization chamber. A liquid sterilant is vaporized and delivered into the carrier gas flow entering the chamber, and then converted to a form suitable for disposal after exiting the chamber, i.e., water and oxygen in the case of hydrogen peroxide sterilant.

The method succeeds in optimizing sterilization by monitoring the chamber temperature, relative humidity, and vapor concentration. The carrier gas is then only partially and selectively dried in response to these parameters to maintain a predetermined percent of sterilant vapor saturation in the sterilization chamber. Percent saturation is defined as the ratio between actual sterilant vapor concentration and the sterilant vapor dewpoint concentration.

In the method of the present invention, the water vapor concentration of the carrier gas entering the chamber may be higher than was previously obtained or desired. Yet, superior kill potentials and more efficient sterilization can be obtained.

Figure 1:
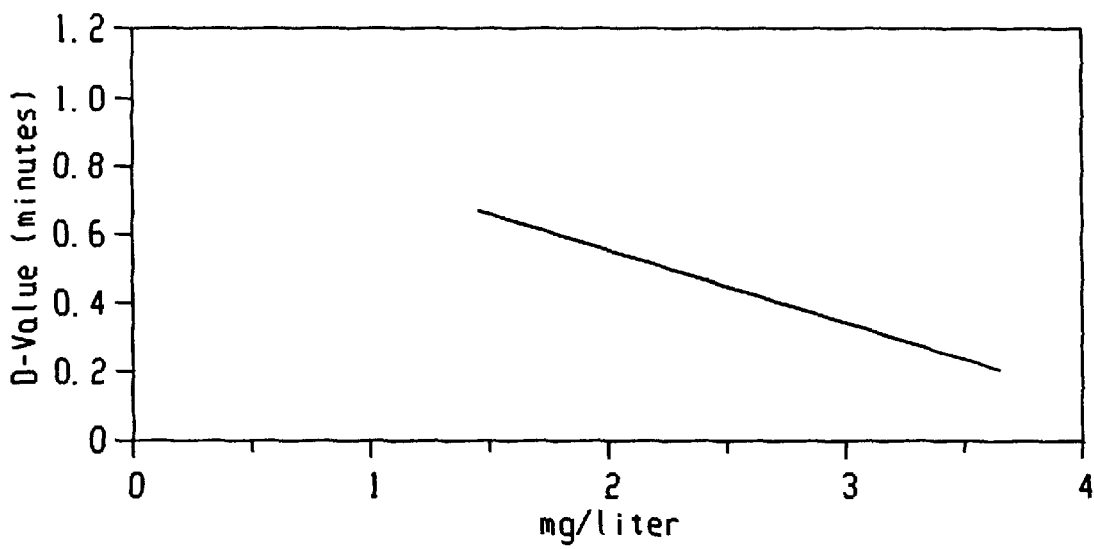
FIG. 1 is a graph showing exemplary D-values of a range of hydrogen peroxide concentrations.
Figure 2:
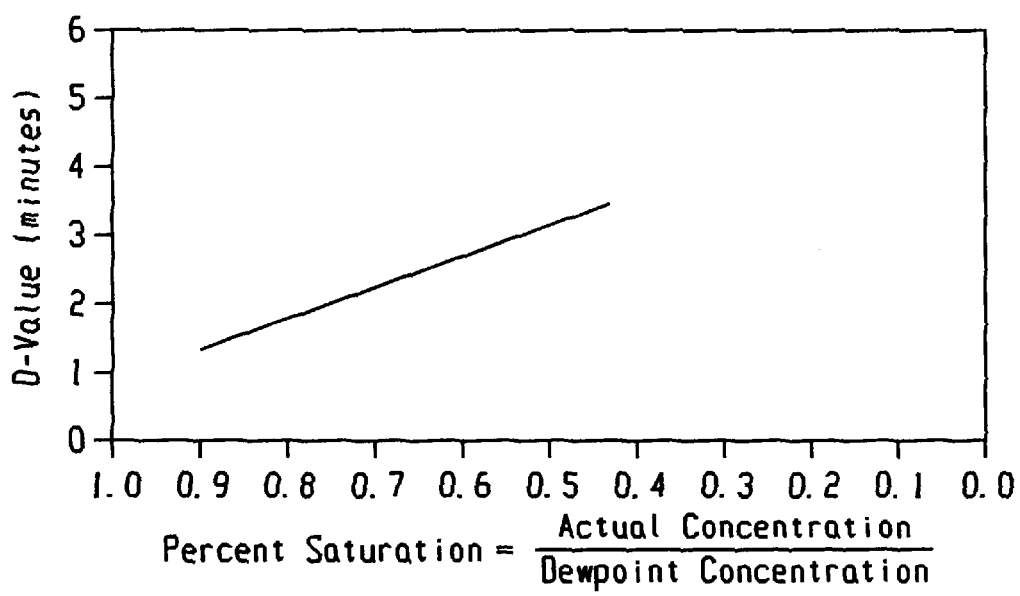
FIG. 2 is a graph showing exemplary D-values of a range of hydrogen peroxide percent saturations.

The improvement provided by the present invention can be appreciated by inspecting FIGS. 1 and 2. FIG. 1 illustrates the relationship between the D-value for *Bacillus stearothermophilus* and hydrogen peroxide sterilant vapor concentrations ranging from 1.5 mg/l to 3.7 mg/l. The percent saturation is held constant at 80%. As indicated, the sterilization efficacy approximately doubles (the D-value is halved) when the concentration is doubled.

Prior closed, flow-through systems recognized the foregoing relationship and attempted to maximize the concentration of sterilant vapor in the carrier gas flowing into the sterilization chamber. The amount of sterilant that can be injected into a carrier gas is limited, however, by dew point considerations. Table I shows the dewpoint concentrations for 35% hydrogen peroxide that is flash vaporized (as described in U.S. Pat. No. 4,642,165, incorporated by reference herein) into an enclosure with the given temperature and relative humidity air:

TABLE 1

Dewpoint Concentration for $H_2O_2$ Vapor

| Enclosure Temperature | Enclosure Relative Humidity | | | |
|---|---|---|---|---|
| | 0% | 10% | 20% | 30% |
| 15° C. | 1.103 | 0.903 | 0.731 | 0.585 |
| 20° C. | 1.562 | 1.284 | 1.044 | 0.839 |
| 25° C. | 2.184 | 1.805 | 1.477 | 1.185 |
| 30° C. | 3.008 | 2.497 | 2.051 | 1.651 |
| 35° C. | 4.097 | 3.410 | 2.810 | 2.270 |
| 40° C. | 5.485 | 4.599 | 3.803 | 3.081 |

FIG. 2 illustrates the relationship between the D-value for *Bacillus stearothermophilus* and hydrogen peroxide vapor percent saturations ranging from 40 to 90%. The hydrogen peroxide vapor concentration is maintained at 1.6 mg/l. As indicated, the sterilization efficacy nearly quadruples (the D-value goes from 4 to almost 1) when the sterilant vapor percent saturation is slightly more than doubled. By controlling percent saturation independently of concentration, the present invention obtains significantly improved sterilization.

Figure 3:
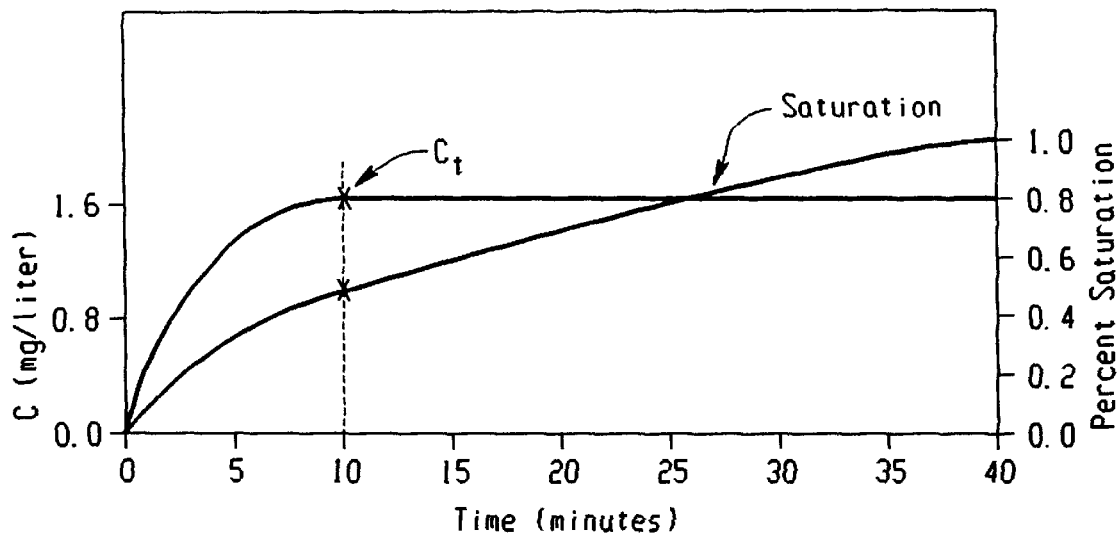
FIG. 3 is a graph showing the sterilant concentrations and sterilant percent saturations over a sterilization cycle for a prior closed, flow-through prior sterilization method, which maintains a predetermined sterilant vapor concentration.
Figure 4:
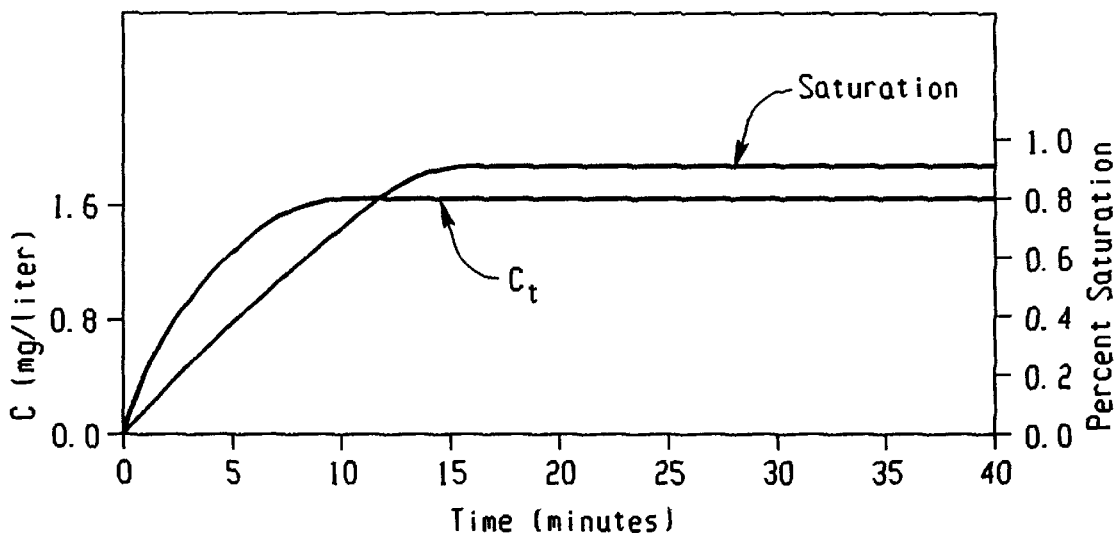
FIG. 4 is a graph showing the sterilant concentrations and sterilant percent saturations over a sterilization cycle for the sterilization method of the present invention, which maintains a predetermined sterilant vapor percent saturation.
Figure 5:
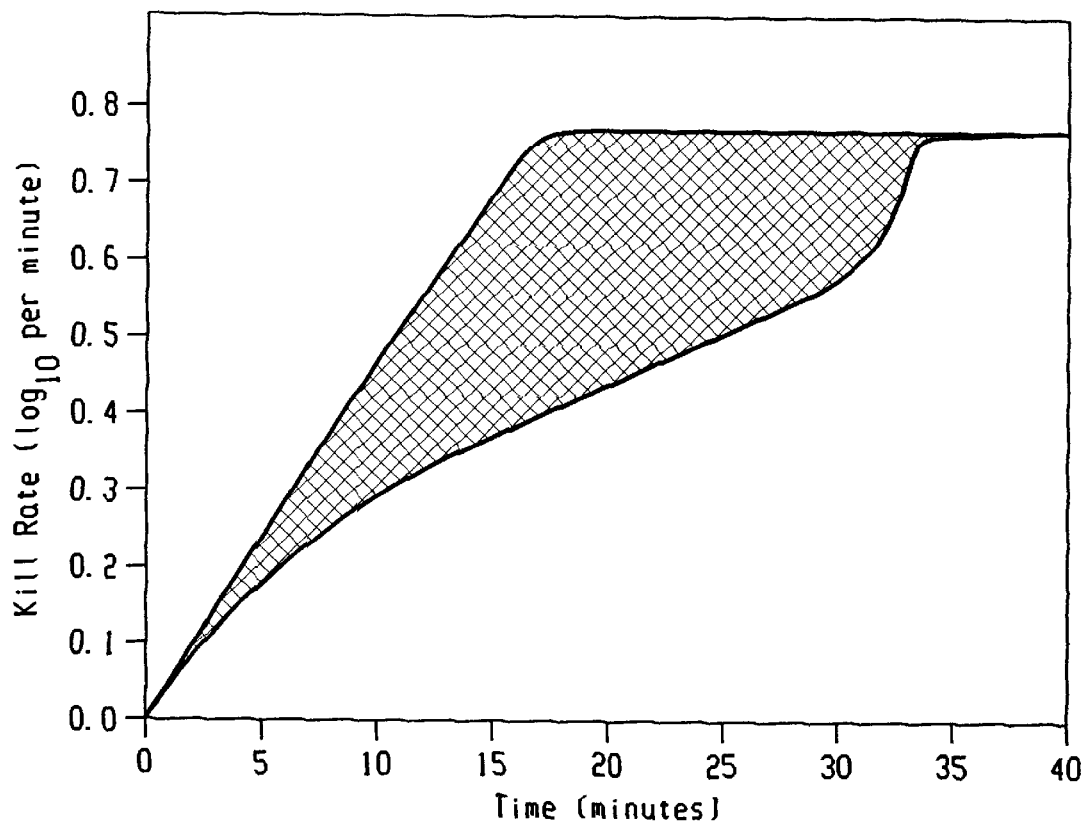
FIG. 5 is a graph comparing the bacterial kill rates over a sterilization cycle for the sterilization methods of FIGS. 3 and 4.

FIGS. 3–5 also illustrate the improved results obtained with the present invention. FIG. 3 illustrates a typical sterilant vapor and percent saturation plot for a prior sterilization cycle which seeks to maximize concentration. FIG. 4 illustrates a typical sterilant vapor and percent saturation plot for the present invention. The percent saturation is below 70% during the first half of the prior sterilization cycle. In the present invention, the percent saturation is only below 70% for the first ten minutes of the sterilization cycle and is at about 90% for most of the cycle.

The kill potential for a sterilization cycle can be determined by plotting the instantaneous kill rate versus time for a sterilization cycle and calculating the area under the curve. Using the D-values from FIG. 2 and the curves from FIGS. 3 and 4, the kill rates for the prior system and the present invention are plotted in FIG. 5. The cross-hatch area shows the significantly improved kill potential for the present invention.

Figure 6:
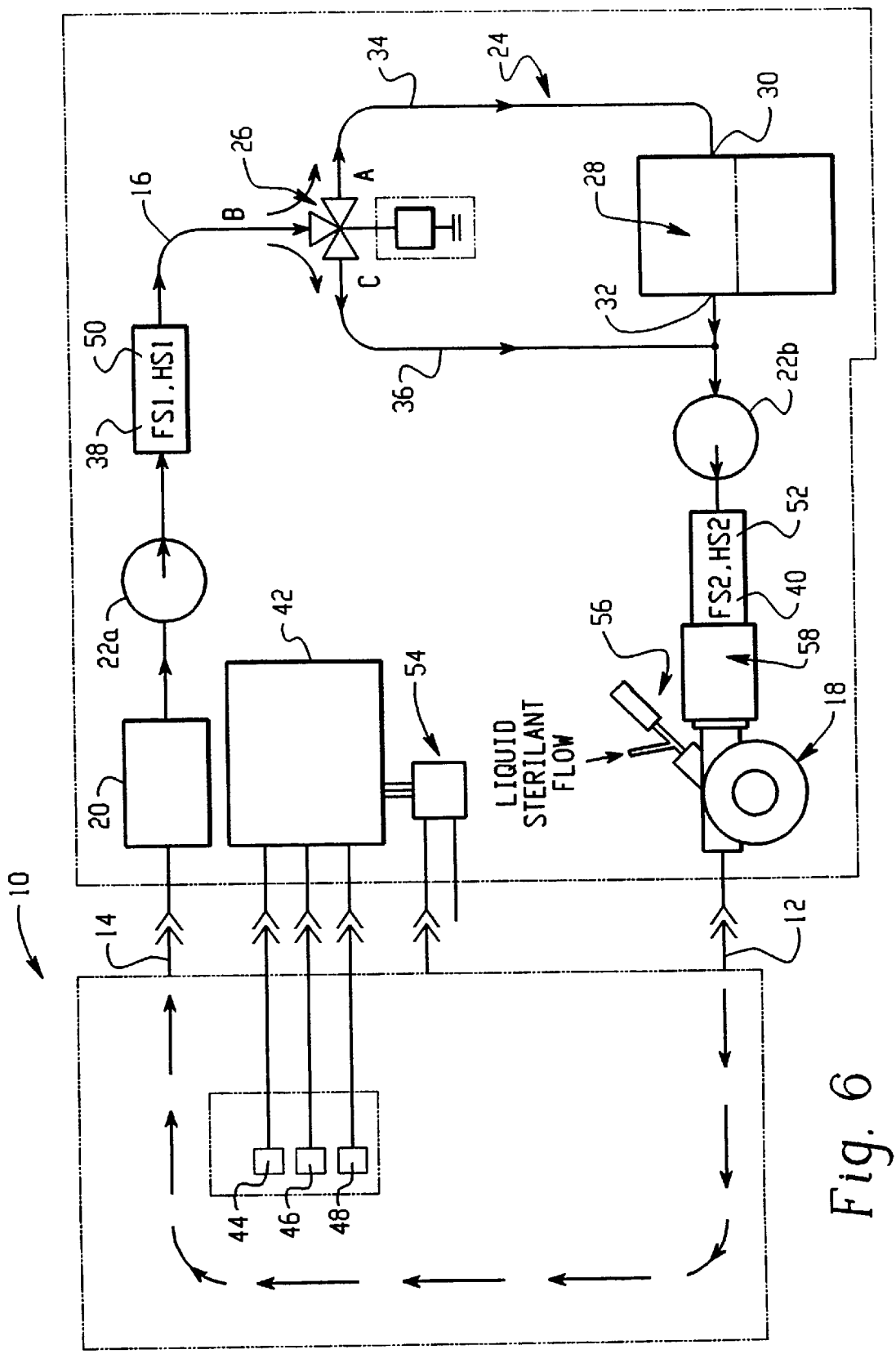
FIG. 6 is a schematic illustration of one embodiment of the continuous-operation, closed-loop flow through system of the present invention.

The method of the invention will now be described with further reference to the exemplary system illustrated in FIG. 6. As shown, the flow-through vapor phase sterilization system of the invention includes a sealable chamber 10 having an inlet port 12 and an outlet port 14. A conduit circuit 16 is fluidly connected to the chamber ports to provide a closed-loop flow path for recirculating a carrier gas into, through, and out of the chamber 10.

The system also includes a liquid sterilant vaporizer unit 18 for delivering a vaporized liquid sterilant into the carrier gas flow. The vaporizer unit 18 is fluidly connected to the conduit circuit between the drying unit and the chamber inlet port. Liquid sterilant is preferably atomized in an atomizer 56 fluidly connected to the vaporizer 18 and delivered to the vaporizer in the form of a fine mist to increase the likelihood of complete vaporization.

In addition, the system includes a converter 20 for converting the sterilant vapor to a form suitable for disposal, and fluidly connected to the conduit circuit downstream of the chamber outlet port 14. When the sterilant vapor is hydrogen peroxide, the converter 20 preferably comprises a catalytic converter for decomposing hydrogen peroxide to water and oxygen.

The system also includes a blowing unit 22a and 22b and an adjustable drying unit 24, each fluidly connected to the conduit circuit. The blowing unit serves to push or force the carrier gas around the closed-loop flow path. The adjustable drying unit serves to dry selectively the carrier gas flow entering the chamber. A heater 58 is fluidly connected to the conduit circuit downstream from the drying unit for controlling the temperature of the carrier gas entering the vaporizer 18.

The drying unit 24 preferably comprises a variable valve 26 having a first flow path A-B and a second flow path B-C, and a regenerative air dryer 28 having an inlet port 30 and an outlet port 32. The air dryer 28 is positioned downstream of the variable valve 26. A first fluid flow line 34 connects the first flow path to the dryer inlet port 30, while a second fluid flow line 36 bypasses the dryer 28 and connects to the conduit circuit downstream of the drying unit. By varying the amount of flow through the first and second valve flow paths, a selected portion of the carrier gas flow can be routed to bypass the dryer 28. In this way, the humidity of the carrier gas can be regulated or adjusted (i.e., the carrier gas can be selectively dried) to maintain a predetermined percent saturation of sterilant vapor in the chamber as the sterilization cycle proceeds.

A first humidity sensor 50 is positioned downstream of the converter 20 to measure the absolute humidity of the air flow exiting the converter 20. A second humidity sensor 52 is positioned downstream of the air dryer 28 to measure the absolute humidity of the air flow exiting the air dryer 28. Assuming, for example, that the air stream exiting the converter has a humidity of 11.5 mg/l and the air dryer reduces the humidity of the air stream that passes through it to 2.3 mg/l, the humidity of the air stream entering the vaporizer can be calculated as reported in Table 2.

TABLE 2

| Fraction Bypassed | Fraction Dried | Air Stream Absolute Humidity (Humidity Sensor 52 reading) | |
|---|---|---|---|
| 0 | 1.0 | 2.3 | mg/liter |
| .1 | .9 | 3.22 | ↓ |
| .2 | .8 | 4.14 | ↓ |
| .3 | .7 | 5.06 | ↓ |
| .4 | .6 | 5.98 | ↓ |
| .5 | .5 | 6.9 | ↓ |
| .6 | .4 | 7.82 | ↓ |
| .7 | .3 | 8.74 | ↓ |
| .8 | .2 | 9.66 | ↓ |
| .9 | .1 | 10.58 | ↓ |
| 1.0 | 0 | 11.5 | ↓ |
| | | | mg/liter |

The blowing unit preferably comprises a first blower 22a positioned upstream and a second blower 22b positioned downstream of the drying unit. More preferably, the blowers can be adjusted based on feedback from flow sensors 38 and 40 to provide a slightly negative or positive pressure within the sterilization chamber 10 as monitored by a pressure transducer 54.

In addition, the system includes a processing unit 42 for monitoring the following three parameters within the sterilization chamber during sterilization: 1) the temperature, 2) the relative humidity, and 3) the sterilant vapor concentration. The processing unit also determines or selects the degree of drying of the carrier gas in response to these three parameters, to maintain a predetermined percent saturation of the sterilant vapor during sterilization.

The processing unit may include a temperature sensor 44, relative humidity sensor 46, and a vapor concentration sensor 48 positioned within the chamber 10 to monitor directly the internal chamber temperature, relative humidity, and vapor concentration. Alternatively, the processing unit may include means for monitoring these parameters indirectly. The vapor concentration can be indirectly monitored through calculations based on the measured air-flow rate and sterilant vapor injection rate. The relative humidity can be indirectly monitored by using the humidity sensor 50 positioned downstream of the converter to measure the absolute humidity of the exiting air flow. The background humidity is subtracted from that value. A standard water vapor dew point chart can then be consulted to provide the relative humidity for the difference at the chamber temperature.

Preferred embodiments of the invention are further illustrated by the following examples, in which an aqueous 35% hydrogen peroxide solution was flash vaporized:

EXAMPLE 1

The chamber temperature is 35° C., relative humidity is 20%, and sterilant vapor concentration is 2.27 mg/l. Reference to Table I or another available dewpoint concentration chart shows that the sterilant dewpoint concentration is 2.810 mg/l. The percent saturation is therefore 80%.

According to the present invention, the humidity of the carrier gas entering the chamber is adjusted by repositioning the variable valve to bypass a larger fraction of air so that the relative humidity of the enclosure becomes 30%. According to the dewpoint concentration chart, the dewpoint concentration is now 2.27 mg/l. The percent saturation then becomes 100%.

EXAMPLE 2

The chamber temperature is 40° C. and the sterilant vapor concentration is 3.081 mg/l, calculated based on the air flow rate and the sterilant delivery rate. Humidity sensor 50 indicates that the absolute humidity in the returning air stream is 15.94 mg/l. For the flash vaporized sterilant, the aqueous solution contributes 10.22 mg/l humidity or (65/35)×3.081 mg/l. Subtracting this value from the absolute humidity results in 15.94−5.72 mg/l=10.22 mg/l background humidity. Referring to a dewpoint chart, at 40° C. this results in 20% relative humidity. At 40° C. and 20% relative humidity the sterilant vapor dewpoint concentration is 3.803 mg/l. This means that the calculated percent saturation is 81%.

The variable valve is repositioned to bypass a larger fraction of air flow around the air dryer. The background humidity in the returning air stream at dewpoint conditions at 40° C. for a 3.081 mg/l hydrogen peroxide vapor concentration according to Table 1 is 30%. The absolute humidity corresponding to a 30% background relative humidity is found as follows:

AH=(65/35)×3.081 mg/l plus 15.35 mg/l=21.08 mg/l. Repeating the above calculations for the new absolute humidity show that the percent saturation is 100%. Thus, by increasing the carrier gas humidity from 20% to 30% the chamber reaches 100% sterilization, greatly improving the sterilization.

EXAMPLE 3

Blower **22*b* is adjusted based on feedback from the flow sensor 40 to provide an air flow rate of 50 CFM. Blower 22*b* is adjusted to provide a lower air flow rate. The rotational speed of blower 22*a* is increased (or decreased) based upon the reading from the pressure transducer 54**. A slightly positive (0.2 in WC≦P≦2 in WC) pressure is thus maintained in the semi-sealed enclosure while maintaining the desired air flow rate, sterilant vapor concentration and percent saturation.

EXAMPLE 4

Blower **22*a* is adjusted based on feedback from the flow sensor 38 to provide an air flow rate of 50 CFM. Blower 22*b* is adjusted to provide a lower air flow rate. The rotational speed of blower is increased (or decreased) based upon the reading from the pressure transducer 54**. A slightly negative (02 in WC≦P≦−0.13 in WC) pressure is thus maintained in the semi-sealed enclosure while maintaining the desired air flow rate, sterilant vapor concentration and percent saturation.

While the invention has been described herein with reference to the preferred embodiments, it is to be understood that it is not intended to limit the invention to the specific forms disclosed. On the contrary, it is intended to cover all modifications and alternative forms falling within the spirit and scope of the invention.

I claim:

1. A closed-loop, flow through method of vapor phase decontamination in which a carrier gas is selectively and adjustably dried to varying amounts to maintain a predetermined humidity level within a sterilization chamber, which comprises the steps of:

providing a sealable chamber having an inlet port and an outlet port, and a closed-loop conduit circuit having a first end fluidly connected to the chamber inlet port and a second end fluidly connected to the chamber outlet port;

recirculating a flow of a carrier gas into, through, and out of the chamber and around the closed-loop conduit circuit;

delivering a vaporized decontaminant into the recirculating carrier gas flow upstream of the chamber inlet port;

converting the decontaminant vapor to a form suitable for disposal downstream of the chamber outlet port;

monitoring the chamber temperature, the chamber relative humidity, and the decontaminant vapor concentration in the chamber during decontamination;

selectively adjusting an amount of drying of the carrier gas entering the chamber in response to the monitored chamber temperature, chamber relative humidity, and decontaminant vapor concentration to a predetermined humidity level to maintain a predetermined percent saturation of the decontaminant vapor in the chamber during decontamination.

2. A vapor phase decontamination method comprising:

circulating a flow of a carrier gas into, through, and out of a decontamination chamber;

selectively routing a first portion of the carrier gas flow discharged from the decontamination chamber through a dryer and selectively bypassing a second portion of the carrier gas flow around the dryer;

combining the first and second portions of the carrier gas flow;

entraining a decontaminant vapor into the combined carrier gas flow portions upstream of the decontamination chamber;

monitoring a temperature, a relative humidity, and a decontaminant vapor concentration in the decontamination chamber;

selectively adjusting the first portion of the carrier gas flow routed to the dryer relative to the second portion of the carrier gas flow bypassing the dryer in response to the monitored temperature, relative humidity, and decontaminant vapor concentration to control a percent saturation of the decontaminant vapor in the chamber.

3. The method of claim 1, wherein the carrier gas is air.

4. The method of claim 1, wherein the vapor decontaminant comprises hydrogen peroxide.

5. The method of claim 4, wherein the converting step includes catalytically decomposing the hydrogen peroxide vapor into water and oxygen.

6. The method of claim 1, wherein the predetermined percent saturation ranges from about 85% to about 95%.

7. The method of claim 1, wherein the chamber temperature is monitored directly by sensing the read-out from a temperature sensor positioned in the chamber.

8. The method of claim 1, wherein the chamber relative humidity is monitored directly by sensing the read-out from a humidity sensor positioned in the chamber.

9. A closed-loop, flow through method of vapor phase decontamination in a sealable chamber having an inlet port and an outlet port, and a closed-loop conduit circuit having a first end fluidly connected to the chamber inlet port and a second end fluidly connected to the chamber outlet port, the method comprising:

recirculating a flow of a carrier gas into, through, and out of the chamber and around the closed-loop conduit circuit;

entraining a decontaminant vapor into the recirculating carrier gas flow upstream of the chamber inlet port;

converting the decontaminant vapor to a form suitable for disposal downstream of the chamber outlet port;

monitoring temperature and decontaminant vapor concentration in the chamber during decontamination;

monitoring relative humidity of the carrier gas in the chamber indirectly by sensing a read-out from a humidity sensor positioned in the closed-loop conduit circuit downstream of the chamber outlet port;

adjusting a decree of drying the recirculating carrier gas flow in response to the monitored temperature, relative humidity, and decontaminant vapor concentration to maintain a selected percent saturation of the decontaminant vapor in the chamber during decontamination.

10. The method of claim 1, wherein the decontaminant vapor concentration is monitored indirectly and the monitoring step comprises monitoring the carrier gas flow rate and the delivery rate of the decontaminant vapor into the carrier gas.

11. A closed-loop, flow-through vapor phase decontamination system comprising:

a sealable chamber having an inlet port and an outlet port;

a closed-loop conduit circuit having a first end fluidly connected to the chamber inlet port and a second end fluidly connected to the chamber outlet port for recirculating a carrier gas flow into, through, and out of the chamber;

a blowing unit fluidly connected to the conduit circuit to recirculate the carrier gas;

a drying unit fluidly connected to the conduit circuit for drying the carrier gas the drying unit being selectively controllable to adjust a decree to which humidity of the carrier gas is reduced;

a vaporizer unit fluidly connected to the conduit circuit between the drying unit and the chamber inlet port for delivering a decontaminant vapor into the recirculating carrier gas flow;

a converter for converting the decontaminant vapor to a form suitable for disposal, fluidly connected to the conduit circuit downstream of the chamber outlet port;

a processing unit for monitoring instantaneous temperature, relative humidity, and decontaminant vapor concentration, and for controlling the adjustable drying unit to adjust the degree of drying of the carrier gas in accordance with the monitored temperature, relative humidity, and concentration to maintain a predetermined percent saturation of the decontaminant vapor in the chamber during decontamination even as any of the temperature, relative humidity, and concentration in the chamber varies.

12. The system of claim 11, wherein the drying unit comprises: an adjustable proportioning valve having a first flow path and a second flow path through which adjustable portions of the recirculating carrier gas are passed, a regenerative driving agent positioned downstream of the proportioning valve and having an inlet port and an outlet port, a first flow line fluidly connecting the first flow path to the regenerative driving agent inlet port, and a second flow line fluidly connecting the second flow path to the conduit circuit between the regenerative drying agent and the vaporizer unit and bypassing the air dryer.

13. The system of claim 11, wherein the blowing unit comprises a first air blower positioned upstream of the drying unit and a second air blower positioned downstream of the drying unit.

14. The system of claim 11, wherein the processing unit comprises a temperature sensor positioned in the chamber.

15. The system of claim 11, wherein the processing unit comprises a relative humidity sensor positioned in the chamber.

16. The system of claim 11, wherein the processing unit comprises a sensor for indicating the absolute humidity of the carrier gas flow exiting the outlet port of the chamber.

17. The system of claim 11, wherein the processing unit comprises a flow meter for the carrier gas and means for determining the delivery rate of the decontaminant vapor into the carrier gas.

18. The system of claim 11, wherein the decontaminant vapor is hydrogen peroxide and the converter comprises a catalytic converter for decomposing hydrogen peroxide to water and oxygen.

* * * * *